United States Patent [19]

Rajagopalan

[11] Patent Number: 5,384,108
[45] Date of Patent: Jan. 24, 1995

[54] MAGNETIC RESONANCE IMAGING AGENTS

[75] Inventor: Raghavan Rajagopalan, Maryland Heights, Mo.

[73] Assignee: Mallinckrodt Medical, Inc., St. Louis, Mo.

[21] Appl. No.: 341,978

[22] Filed: Apr. 24, 1989

[51] Int. Cl.[6] .............................................. A61K 49/00
[52] U.S. Cl. ........................................ 424/9; 436/81; 436/83; 436/84; 514/188; 534/16; 540/546; 544/58.4; 544/59; 544/78; 544/224; 544/225; 544/386; 546/190; 548/518; 556/61; 556/62; 556/63; 556/42; 556/44; 556/55; 556/56; 556/57
[58] Field of Search ............... 564/148, 151; 544/58.4, 544/59, 78, 224, 225, 386; 546/190; 548/518, 106, 403; 514/188; 424/9; 436/81, 83, 84; 534/16; 540/541; 556/62, 63, 61, 42, 44, 55, 56, 57

[56] References Cited

U.S. PATENT DOCUMENTS

| | | | |
|---|---|---|---|
| 3,351,658 | 11/1967 | Borsworth | 562/565 |
| 3,507,892 | 4/1970 | Borsworth | 562/565 |
| 3,565,813 | 2/1971 | Borsworth | 562/565 |
| 3,787,482 | 1/1974 | Borsworth | 562/565 |
| 4,647,447 | 3/1987 | Gries et al. | 424/9 |
| 4,687,658 | 8/1987 | Quay | 424/9 |
| 4,687,659 | 8/1987 | Quay | 424/9 |
| 4,826,673 | 5/1989 | Dean et al. | 424/9 |

FOREIGN PATENT DOCUMENTS

| | | | |
|---|---|---|---|
| 1242643 | 10/1988 | Canada . | |
| 45083 | 1/1966 | German Dem. Rep. | 562/566 |
| 3324235 | 1/1983 | Germany . | |
| 3324236 | 1/1985 | Germany . | |

OTHER PUBLICATIONS

Brasch, et al. Amer. Roentgen Ray Soc. Mar. 1984, pp. 625–630.
Damadian, Science, Mar. 1971 pp. 1151–1153.
Lauterbur, Nature, Mar., 1973, pp. 190–191.
Weinmann, et al American J. Radiology—Mar., 1984 pp. 619–624.
The Merck Index 11th Ed. (Merck and Co., Rahway, N.J., 1989) p. 172.
Grant & Hack's Chemical Dictionary, Fifth Edition, 1987.
Organic Chemistry, Second Edition, 1980, (p. 810).

Primary Examiner—Robert T. Bond
Attorney, Agent, or Firm—Rothwell, Figg, Ernst & Kurz

[57] ABSTRACT

Novel magnetic resonance imaging agents comprise complexes of paramagnetic ions with hydrazide derivatives of polyaminocarboxylic acid chelating agents. The complexes are represented by the formula of:

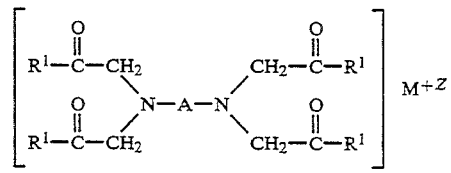

wherein A is $-CHR^2-CHR^3-$ or

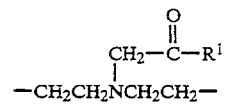

$M^{+Z}$ is a paramagnetic ion of an element with an atomic number of 21–29, 42–44 58–70, and a valence, Z, of +2 or +3; $R^1$ groups may be the same or different and are selected from the group consisting of $-O^-$ and

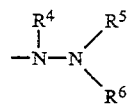

The $R^4$, $R^5$ and $R^6$ groups are as defined in the disclosure. These novel imaging agents are characterized by excellent NMR image-contrasting properties and by
(Abstract continued on next page.)

high solubilities in physiological solutions. A novel method of performing an NMR diagnostic procedure involves administering to a warm-blooded animal an effective amount of a complex as described above and then exposing the warm-blooded animal to an NMR imaging procedure, thereby imaging at least a portion of the body of the warm-blooded animal.

19 Claims, No Drawings

MAGNETIC RESONANCE IMAGING AGENTS

BACKGROUND OF THE INVENTION

This invention relates to nuclear magnetic resonance (NMR) imaging and, more particularly, to methods and compositions for enhancing NMR imaging.

The recently developed technique of NMR imaging encompasses the detection of certain atomic nuclei utilizing magnetic fields and radio-frequency radiation. It is similar in some respects to x-ray computed tomography (CT) in providing a cross-sectional display of the body organ anatomy with excellent resolution of soft tissue detail. As currently used, the images produced constitute a map of the proton density distribution and/or their relaxation times in organs and tissues. The technique of NMR imaging is advantageously non-invasive as it avoids the use of ionizing radiation.

While the phenomenon of NMR was discovered in 1945, it is only relatively recently that it has found application as a means of mapping the internal structure of the body as a result of the original suggestion of Lauterbur (Nature, 242, 190-191 (1973)). The fundamental lack of any known hazard associated with the level of the magnetic and radio-frequency fields that are employed renders it possible to make repeated scans on vulnerable individuals. In addition to standard scan planes (axial, coronal, and sagittal), oblique scan planes can also be selected.

In an NMR experiment, the nuclei under study in a sample (e.g. protons) are irradiated with the appropriate radio-frequency (RF) energy in a highly uniform magnetic field. These nuclei, as they relax, subsequently emit RF at a sharp resonance frequency. The resonance frequency of the nuclei depends on the applied magnetic field.

According to known principles, nuclei with appropriate spin, when placed in an applied magnetic field (B, expressed generally in units of gauss or Tesla ($10^4$ gauss)) align in the direction of the field. In the case of protons, these nuclei precess at a frequency, f, of 42.6 MHz at a field strength of 1 Tesla. At this frequency, an RF pulse of radiation will excite the nuclei and can be considered to tip the net magnetization out of the field direction, the extent of this rotation being determined by the pulse duration and energy. After the RF pulse, the nuclei "relax" or return to equilibrium with the magnetic field, emitting radiation at the resonant frequency. The decay of the emitted radiation is characterized by two relaxation times, i.e., $T_1$, the spin-lattice relaxation time or longitudinal relaxation time, that is, the time taken by the nuclei to return to equilibrium along the direction of the externally applied magnetic field, and $T_2$, the spin-spin relaxation time associated with the dephasing of the initially coherent precession of individual proton spins. These relaxation times have been established for various fluids, organs and tissues in different species of mammals.

In NMR imaging, scanning planes and slice thicknesses can be selected. This selection permits high quality transverse, coronal and sagittal images to be obtained directly. The absence of any moving parts in NMR imaging equipment promotes a high reliability. It is believed that NMR imaging has a greater potential than CT for the selective examination of tissue characteristics in view of the fact that in CT, x-ray attenuation coefficients alone determine image contrast, whereas at least five separate variables ($T_1$, $T_2$, proton density, pulse sequence and flow) may contribute to the NMR signal. For example, it has been shown (Damadian, Science, 171, 1151 (1971)) that the values of the $T_1$ and $T_2$ relaxation in tissues are generally longer by about a factor of 2 in excised specimens of neoplastic tissue compared with the host tissue.

By reason of its sensitivity to subtle physicochemical differences between organs and/or tissues, it is believed that NMR may be capable of differentiating different tissue types and in detecting diseases which induce physicochemical changes that may not be detected by x-ray or CT which are only sensitive to differences in the electron density of tissue.

As noted above, two of the principal imaging parameters are the relaxation times, $T_1$ and $T_2$. For protons (or other appropriate nuclei), these relaxation times are influenced by the environment of the nuclei (e.g., viscosity, temperature, and the like). These two relaxation phenomena are essentially mechanisms whereby the initially imparted radiofrequency energy is dissipated to the surrounding environment. The rate of this energy loss or relaxation can be influenced by certain other nuclei which are paramagnetic. Chemical compounds incorporating these paramagnetic nuclei may substantially alter the $T_1$ and $T_2$ values for nearby protons. The extent of the paramagnetic effect of a given chemical compound is a function of the environment within which it finds itself.

In general, paramagnetic divalent or trivalent ions of elements with an atomic number of 21 to 29, 42 to 44 and 58 to 70 have been found effective as NMR image contrasting agents. Suitable such ions include chromium (III), manganese (II), manganese (III), iron (III), iron (II), cobalt (II), nickel (II), copper (II), praseodymium (III), neodymium (III), samarium (III) and ytterbium (III). Because of their very strong magnetic moments, gadolinium (III), terbium (III), dysprosium (III), holmium (III) and erbium (III) are preferred. Gadolinium (III) ions have been particularly preferred as NMR image contrasting agents.

Typically, the divalent and trivalent paramagnetic ions have been administered in the form of complexes with organic complexing agents. Such complexes provide the paramagnetic ions in a soluble, non-toxic form, and facilitate their rapid clearance from the body following the imaging procedure. Gries et al., U.S. Pat. No. 4,647,447, disclose complexes of various paramagnetic ions with conventional aminocarboxylic acid complexing agents. A preferred complex disclosed by Gries et al. is the complex of gadolinium (III) with diethylenetriaminepentaacetic acid ("DTPA"). This complex may be represented by the formula:

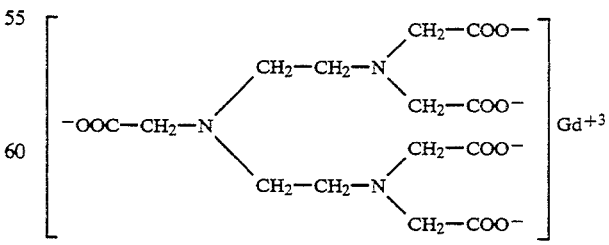

Paramagnetic ions, such as gadolinium (III), have been found to form strong complexes with DTPA. These complexes do not dissociate substantially in physiological aqueous fluids. The complexes have a net charge of −2, and generally are administered as soluble salts. Typical such salts are the sodium and N-methylglucamine salts.

The administration of ionizable salts is attended by certain disadvantages. These salts can raise the in vivo ion concentration and cause localized disturbances in osmolality, which in turn, can lead to edema and other undesirable reactions.

Efforts have been made to design non-ionic paramagnetic ion complexes. In general, this goal has been achieved by converting one or more of the free carboxylic acid groups of the complexing agent to neutral, non-ionizable groups. For example, S. C. Quay, in U.S. Pat. Nos. 4,687,658 and 4,687,659, discloses alkylester and alkylamide derivatives, respectively, of DTPA complexes. Similarly, published West German applications P 33 24 235.6 and P 33 24 236.4 disclose mono- and polyhydroxyalkylamide derivatives of DTPA and their use as complexing agents for paramagnetic ions.

The nature of the derivative used to convert carboxylic acid groups to non-ionic groups can have a significant impact on tissue specificity. Hydrophilic complexes tend to concentrate in the interstitial fluids, whereas lipophilic complexes tend to associate with cells. Thus, differences in hydrophilicity can lead to different applications of the compounds. See, for example, Weinmann et al., *AJR*, 142, 679 (March 1984) and Brasch et al., *AJR*, 142, 625 (March 1984).

Thus, a need continues to exist for new and structurally diverse non-ionic complexes of paramagnetic ions for use as NMR imaging agents. There is further a need in the art to develop highly stable complexes with good relaxivity characteristics.

SUMMARY OF THE INVENTION

The present invention provides novel complexing agents and complexes of complexing agents with paramagnetic ions. The complexes are represented by the following formula:

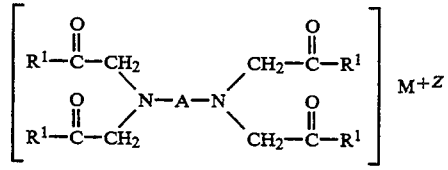

wherein A is —CHR$^2$—CHR$^3$— or

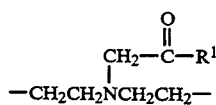

M$^{+Z}$ is a paramagnetic ion of an element with an atomic number of 21–29, 42–44 or 58–70, and a valence, Z, of +2 or +3; R$^1$ groups may be the same or different and are selected from the group consisting of —O$^-$ and

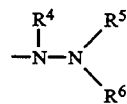

wherein R$^4$, R$^5$, and R$^6$ may be the same or different and are hydrogen, alkyl, hydroxyalkyl, alkoxyalkyl, aminoalkyl or acylaminoalkyl wherein the carbon-containing portions contain from 1 to about 6 carbon atoms, or R$^5$ and R$^6$ can together with the adjacent nitrogen form a heterocyclic ring of five, six or seven members, wherein 0 or 1 members other than the nitrogen are —O—, —S—,

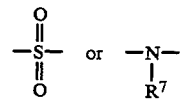

and which members are unsubstituted or substituted by hydroxy, alkyl, aryl, hydroxyalkyl, aminoalkyl, aminoaryl, alkylamino, or carbamoyl Wherein the substituents contain from 1 to about 6 carbon atoms, or R$^4$ and R$^5$ can together with the nitrogens to which each is attached form a hetercyclic ring of five, six or seven members, wherein 0 to 1 members other than the nitrogens are

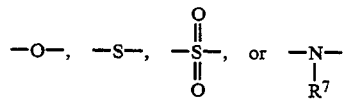

and which members are unsubstituted or substituted by hydroxy, alkyl, aryl, hydroxyalkyl, aminoalkyl, aminoaryl, alkylamino, or carbamoyl wherein the substituents contain from 1 to about 6 carbon atoms;

R$^2$ and R$^3$ may be the same or different and are hydrogen, alkyl having from 1 to about 6 carbon atoms, phenyl or benzyl;

R$^7$ is hydrogen, alkyl, hydroxyalkyl, alkoxyalkyl, aminoalkyl or acylaminoalkyl wherein the carbon-containing portions contain from 1 to about 6 carbon atoms;

and wherein 2 or 3 of the R$^1$ groups are —O$^-$ and the remainder of the R$^1$ groups are

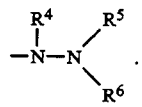

In one embodiment, R$^5$ and R$^6$ together form a heterocyclic ring of the formula

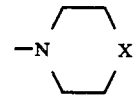

wherein X is a single bond,

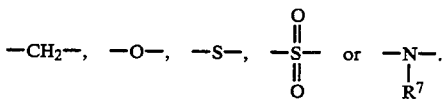

In other embodiments, wherein R$^4$ and R$^5$ together with the nitrogens to which each is attached form a heterocyclic ring, the heterocyclic ring may have the formula

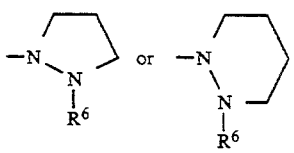

wherein $R^6$ is as defined above.

Also disclosed is a method of performing an NMR diagnostic procedure which involves administering to a warm-blooded animal an effective amount of the above-described complex and then exposing the warm-blooded animal to an NMR imaging procedure, thereby imaging at least a portion of the body of the warm-blooded animal.

DETAILED DESCRIPTION OF THE INVENTION

The complexing agents employed in this invention are derivatives of well-known polyaminocarboxylic acid chelating agents, such as DTPA and ethylenediaminetetraacetic acid ("EDTA"). In these derivatives, some carboxylic acid groups of the polyaminocarboxylic acid are converted to hydrazide groups, such as those of the formula,

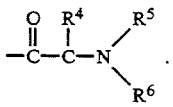

Thus, if the paramagnetic ion is trivalent and the chelating agent is DTPA, two of the carboxylic acid groups will be derivatized to the hydrazide form. Likewise, if the paramagnetic ion is divalent, three of the carboxylic acid groups of DTPA or two of the carboxylic acid groups of EDTA will be derivatized to the hydrazide form. When reacted with a divalent or trivalent paramagnetic ion, the resulting complexes are substantially non-ionic as evidenced by very low electrical conductivity.

The hydrazide derivatives of the chelating agents are prepared in a conventional manner. One process for preparing hydrazide derivatives is set forth in U.S. Pat. No. 3,787,482. In general, they are prepared by reacting a stoichiometric amount of a mono-, di-, or tri-substituted hydrazino compound of the formula

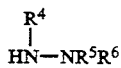

with a reactive derivative of the polyaminocarboxylic acid chelating agent under hydrazide-forming conditions. Such reactive derivatives include, for example, anhydrides, mixed anhydrides and acid chlorides. As noted above, $R^5$ and $R^6$ together with the adjacent nitrogen may form a heterocyclic ring of five, six or seven members. This embodiment results in compounds containing a hydrazide functional group external to the ring structure. In another embodiment, $R^4$ and $R^5$ together with the nitrogens to which each is attached form a heterocyclic ring of five, six or seven members. In this embodiment, the hydrazide functional group is internal to the ring structure. This ring can be saturated or unsaturated and substituted or unsubstituted. If the heterocyclic ring is substituted, the total number of substituents typically is 1 to 3. Examples of suitable heterocyclic rings include pyrrolidinyl, pyrrolyl, pyrazolidinyl, pyrazolinyl, pyridyl, piperidyl, piperazinyl, morpholinyl, etc.

In one embodiment, the reactions for preparing the hydrazide derivatives of the present invention are conducted in an organic solvent at an elevated temperature. Suitable solvents include those in which the reactants are sufficiently soluble and which are substantially unreactive with the reactants and products. Lower aliphatic alcohols, ketones, ethers, esters, chlorinated hydrocarbons, benzene, toluene, xylene, lower aliphatic hydrocarbons, and the like may advantageously be used as reaction solvents. Examples of such solvents are methanol, ethanol, n-propanol, isopropanol, butanol, pentanol, acetone, methylethyl ketone, diethylketone, methyl acetate, ethyl acetate, chloroform, methylene chloride, dichloroethane, hexane, heptane, octane, decane, and the like. If a DTPA or EDTA-type acid chloride is used as the starting material, then the reaction solvent advantageously is one which does not contain reactive functional groups, such as hydroxyl groups, as these solvents can react with the acid chlorides, thus producing unwanted by-products.

The reaction temperature may vary widely, depending upon the starting materials employed, the nature of the reaction solvent and other reaction conditions. Such reaction temperatures may range, for example, from about 20° C. to about 85° C., preferably from about 25° C. to about 50° C.

Following reaction of the reactive polyaminocarboxylic acid derivatives with the hydrazine compound, any remaining anhydride or acid chloride groups can be hydrolyzed to the carboxylate groups by adding a stoichiometric excess of water to the reaction mixture and heating for a short time.

The resulting hydrazide is recovered from the reaction mixture by conventional procedures. For example, the product may be precipitated by adding a precipitating solvent to the reaction mixture, and recovered by filtration or centrifugation.

The paramagnetic ion is combined with the hydrazide under complex-forming conditions. In general, any of the paramagnetic ions referred to above can be employed in making the complexes of this invention. The complexes can conveniently be prepared by mixing a suitable oxide or salt of the paramagnetic ion with the complexing agent in aqueous solution. To assure complete complex formation, a slight stoichiometric excess of the complexing agent may be used. In addition, an elevated temperature, e.g., ranging from about 20° C. to about 100° C., preferably from about 40° C. to about 80° C., may be employed to insure complete complex formation. Generally, complete complex formation will occur within a period from a few minutes to a few hours after mixing. The complex may be recovered by precipitation using a precipitating solvent such as acetone, and further purified by crystallization, if desired.

The novel complexes of this invention can be formulated into diagnostic compositions for enteral or parenteral administration. These compositions contain an effective amount of the paramagnetic ion complex along with conventional pharmaceutical carriers and excipients appropriate for the type of administration contemplated. For example, parenteral formulations advantageously contain a sterile aqueous solution or suspension of from about 0.05 to 1.0M of a paramagnetic ion complex according to this invention. Preferred parenteral formulations have a concentration of paramagnetic ion complex of 0.1M to 0.5M. Such solutions also may contain pharmaceutically acceptable buffers and, optionally, electrolytes such as sodium chloride. The compositions may advantageously contain a slight excess, e.g., from about 0.1 to about 15 mole % excess, of the complexing agent or its complex with a physiologically acceptable, non-toxic cation to insure that all of the potentially toxic paramagnetic ion is complexed. Such physiologically acceptable, non-toxic cations include calcium ions, magnesium ions, copper ions, zinc ions and the like. Calcium ions are preferred. A typical single dosage formulation for parenteral administration has the following composition:

| | |
|---|---|
| Gadolinium DTPA-bis(hydrazide) | 330 mg/ml |
| Calcium DTPA-bis(hydrazide) | 14 mg/ml |
| Distilled Water | q.s. to 1 ml |
| pH | 7.0 |

Parenteral compositions may be injected directly or mixed with a large volume parenteral composition for systemic administration.

Formulations for enteral administration may vary widely, as is well-known in the art. In general, such formulations are liquids which include an effective amount of the paramagnetic ion complex in aqueous solution or suspension. Such enteral compositions may optionally include buffers, surfactants, thixotropic agents, and the like. Compositions for oral administration may also contain flavoring agents and other ingredients for enhancing their organoleptic qualities.

The diagnostic compositions are administered in doses effective to achieve the desired enhancement of the NMR image. Such doses may vary widely, depending upon the particular paramagnetic ion complex employed, the organs or tissues which are the subject of the imaging procedure, the NMR imaging equipment being used, etc. In general, parenteral dosages will range from about 0.01 to about 1.0 MMol of paramagnetic ion complex per kg of patient body weight. Preferred parenteral dosages range from about 0.05 to about 0.5 MMol of paramagnetic ion complex per kg of patient body weight. Enteral dosages generally range from about 0.5 to about 100 MMol, preferably from about 1.0 to about 20 MMol of paramagnetic ion complex per kg of patient body weight.

The novel NMR image contrasting agents of this invention possess a unique combination of desirable features. The paramagnetic ion complexes exhibit an unexpectedly high solubility in physiological fluids, notwithstanding their substantially non-ionic character. This high solubility allows the preparation of concentrated solutions, thus minimizing the amount of fluid required to be administered. The non-ionic character of the complexes also reduces the osmolality of the diagnostic compositions, thus preventing undesired edema and other side effects. As illustrated by the data presented below, the compositions of this invention have very low toxicities, as reflected by their high $LD_{50}$ values.

The diagnostic compositions of this invention are used in the conventional manner. The compositions may be administered to a warm-blooded animal either systemically or locally to the organ or tissue to be imaged, and the animal then subjected to the NMR imaging procedure. The compositions have been found to enhance the magnetic resonance images obtained by these procedures. In addition to their utility in magnetic resonance imaging procedures, the complexing agents of this invention may also be employed for delivery of radiopharmaceuticals or heavy metals for x-ray contrast into the body.

The invention is further illustrated by the following examples, which are not intended to be limiting.

EXAMPLE I

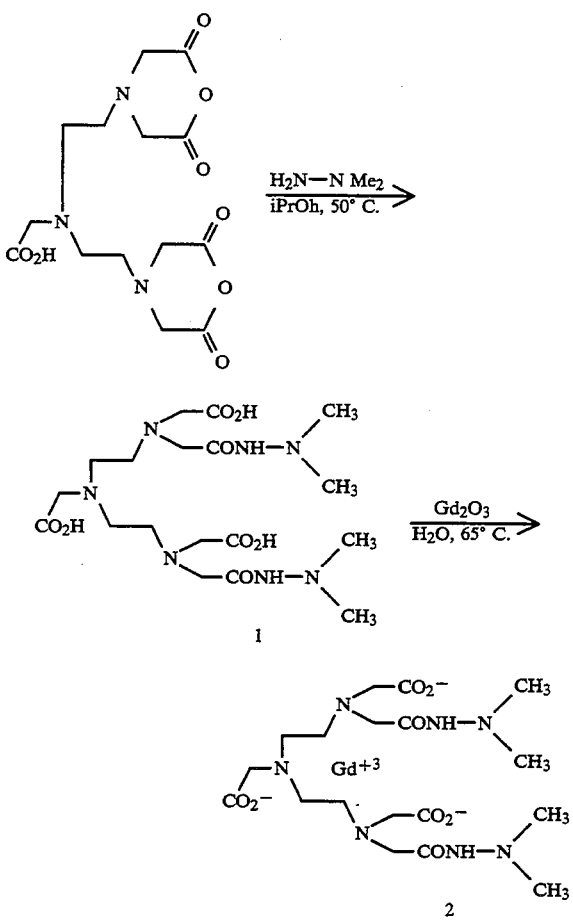

Preparation of [N,N''-Bis(2,2-dimethylhydrazino)carbamoylmethyl]diethylene-triamine-N,N',N''-triacetic acid:

A mixture of DTPA-dianhydride (10 g) and N,N-dimethylhydrazine (3.7 g) in isopropanol (25 mL) was stirred at 50° C. (water bath) for 18 hours. The gummy residue was dissolved by the addition of 50 mL of methanol and the solution filtered through a fine porosity sintered glass funnel to remove undissolved impurities. The solvent was removed under reduced pressure and the solid was recrystallized from 95% ethanol/isopropanol to give 5.3 g of colorless solid (m.p. 142°–144° C.). Anal. Calcd. for $C_{18}H_{35}N_7O_8 \times 1.5 H_2O$: C, 42.86; H, 7.54; N, 19.44. Found: C, 43.03; H, 7.52; N, 18.91.

Preparation of [N,N'-Bis(2,2-dimethylhydrazino)carbonylmethyl]diethylenetriamine-N,N',N''-triaceto]-gadolinium (III) hydrate (MP-1291).

A mixture of the ligand (9.4 g) and gadolinium oxide (3.3 g) in deionized, distilled water (50 mL) was heated at 65°–70° C. for 20 hours. The pale green solution was filtered through a fine porosity sintered glass funnel to remove undissolved impurities. The clear filtrate was then poured onto acetone (1 L) and the solid was collected and dried. The off white solid was redissolved in water (25 mL) and purified by flash chromatography over reverse phase (octadecylsilane derivatized silica gel) sorbent to give almost colorless solid. Yield 10.3 g (88%). Anal. Calcd. for $C_{18}H_{32}N_7O_8Gd \times H_2O$. C, 31.79; H, 4.91; N, 11.58; Gd, 26.01. Found: C, 31.89; H, 4.89; N, 11.45; Gd, 25.70.

EXAMPLE II

The acute intravenous toxicity of the compound of Example 1 was determined as follows: ICR mice, at 1 to 4 per dose level, received single intravenous injections of the test substance via a lateral tail vein at the rate of approximately 1 ml/minute. The test substances were at concentrations chosen to result in dose volumes of 5 to 75 ml/kg body weight. Dosing began at a volume of 10 ml/kg. Dose adjustments up or down were made to closely bracket the estimated $LD_{50}$ with 4 animals per group (2 males and 2 females). Observations of the mice were recorded at times 0, 0.5, 1, 2, 4 and 24 hours and once daily thereafter for up to 7 days post injection. On the 7th day post injection, the mice were euthanized, weighed and necropsied. Abnormal tissues were noted. At this time a decision was made as to whether any histopathology was to be performed and whether or not the tissues should be retained. Necropsies were also performed on mice expiring after 24 hours post-injection, except for dead mice found on the weekends. The $LD_{50}$ values, along with 95% CI were calculated using a modified Behrens-Reed-Meunch method. The results for the complex of Example 1 are reported below:

$LD_{50}$: 11.5 mmol/kg
95% Confidence Limits: 6.8–19.6 mmol/kg
Sex and Weight Range of Mice: Males (15.5–22.7 g)
Females (19.6–20.3 g)

EXAMPLE III $T_1$ relaxation times were measured using spin-echo sequence on the JEOL FX90Q (90 MHz) FT-NMR spectrometer/Twenty millimolar solution of the complex in Example 1 was prepared in $H_2O/D_2O$ (4:1) mixture and was serially diluted to lower concentrations (10, 5, 2.5, 1.25, 0.526 mM) with $H_2O/D_2O$ (4:1) mixture. $T_1$ measurements were made at each of these 6 concentrations. The relaxivity ($R_1$) was determined by applying least-square fit to the plot of $1/T_1$ versus concentration. The relaxivity of the complex in Example 1 was $4.85+0.06$ $mM^{-1}sec^{-1}$. The correlation coefficient for the least squares analysis was 0.9994.

I claim:

1. A complex having the following formula:

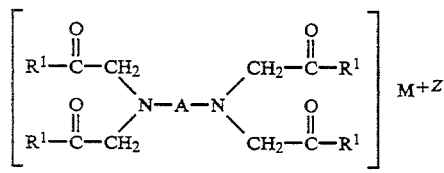

wherein A is —$CHR^2$—$CHR^3$ or

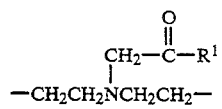

$M^{+Z}$ is a paramagnetic ion of an element with an atomic number of 58–70, and a valence, Z, of +2 or +3; $R^1$ groups may be the same or different and are selected from the group consisting of —$O^-$ and

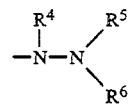

wherein $R^4$, $R^5$ and $R^6$ may be the same or different and are hydrogen, alkyl, hydroxyalkyl, alkoxyalkyl, aminoalkyl or acylaminoalkyl where the carbon-containing portions contain from 1 to about 6 carbon atoms, or $R^5$ and $R^6$ joined together with the adjacent nitrogen form a heterocyclic ring of five, six or seven members, wherein 0 to 1 members other than the nitrogen are

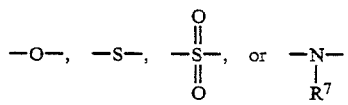

and which members are unsubstituted or substituted by hydroxy, alkyl, aryl, hydroxyalkyl, aminoalkyl, aminoaryl, alkylamino, or carbamoyl, wherein the substituents contain from 1 to about 6 carbon atoms, or $R^4$ and $R^5$ joined together with the nitrogens to which each is attached form a heterocyclic ring of five, six or seven members, wherein 0 or 1 members other than the nitrogens are

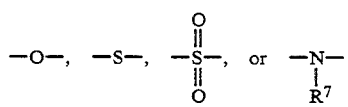

and which members are unsubstituted or substituted by hydroxy, alkyl, aryl, hydroxyalkyl, aminoalkyl, aminoaryl, alkylamino, or carbamoyl wherein the substituents contain from 1 to about 6 carbon atoms;

$R^2$ and $R^3$ may be the same or different and are hydrogen, alkyl having from 1 to about 6 carbon atoms, phenyl or benzyl;

$R^7$ is hydrogen, alkyl, hydroxylalkyl, alkoxyalkyl, aminoalkyl or acylaminoalkyl wherein the carbon-containing portions contain from 1 to about 6 carbon atoms;

and wherein 2 or 3 of the $R^1$ groups are —$O^-$ and the remainder of the $R^1$ groups are

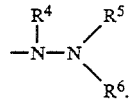

2. The complex of claim 1, wherein A is $$\begin{array}{c} \quad\quad\quad O \\ \quad\quad\quad \| \\ \quad CH_2-C-R^1 \\ \quad | \\ -CH_2CH_2NCH_2CH_2- \end{array}$$

3. The complex of claim 1, wherein A is —CHR²CHR³— and R² and R³ are both hydrogen.

4. The complex of claim 1, wherein $M^{+Z}$ is praseodymium (III), neodymium (III), samarium (III), ytterbium (III), gadolinium (III), terbium (III), dysprosium (III), holmium (III) or erbium (III).

5. The complex of claim 4, wherein $M^{+Z}$ is gadolinium (III), terbium (III), dysprosium (III), holmium (III) or erbium (III).

6. The complex of claim 2, wherein R¹ is dimethylhydrazide and $M^{+Z}$ is gadolinium (III).

7. The complex of claim 1 wherein R⁵ and R⁶ together form a heterocyclic ring of the formula $$-N\diagdown\underset{\diagdown\underline{\quad\quad}\diagup}{\diagup\overline{\quad\quad}\diagdown} X$$

wherein X is a single bond, —CH₂—, —O—, $$\begin{array}{ccc} O & & \\ \| & & \\ -S- & \text{or} & -N- \\ \| & & | \\ O & & R^7 \end{array}$$

8. The complex of claim 7 wherein X is —O—.
9. The complex of claim 7 wherein X is —CH₂—.
10. The complex of claim 7 wherein X is a single bond.
11. The complex of claim 1 wherein R⁴ and R⁵ together form a heterocyclic ring of the formula $$-N\diagdown\underset{\underset{R^6}{|}}{\diagup\overline{\quad}\diagdown}N\diagup \quad \text{or} \quad -N\diagdown\underset{\underset{R^6}{|}}{\diagup\overline{\quad\quad}\diagdown}N\diagup$$

12. A method of performing an NMR diagnostic procedure, which comprises administering to a warm-blooded animal an effective amount of a complex of the formula $$\left[\begin{array}{c} O \quad\quad\quad\quad\quad\quad\quad\quad O \\ \| \quad\quad\quad\quad\quad\quad\quad\quad \| \\ R^1-C-CH_2 \quad\quad\quad\quad CH_2-C-R^1 \\ \diagdown\quad\quad\quad\quad\diagup \\ N-A-N \\ \diagup\quad\quad\quad\quad\diagdown \\ R^1-C-CH_2 \quad\quad\quad\quad CH_2-C-R^1 \\ \| \quad\quad\quad\quad\quad\quad\quad\quad \| \\ O \quad\quad\quad\quad\quad\quad\quad\quad O \end{array}\right] M^{+Z}$$

wherein A is —CHR²—CHR³— or $$\begin{array}{c} \quad\quad\quad O \\ \quad\quad\quad \| \\ \quad CH_2-C-R^1 \\ \quad | \\ -CH_2CH_2NCH_2CH_2- \end{array}$$

$M^{+Z}$ is a paramagnetic ion of an element with an atomic number of 21–29, 42–44, or 58–70, and a valence, Z, of +2 or +3, R¹ groups may be the same or different and are selected from the group consisting of —O⁻ and $$\begin{array}{c} R^4 \quad R^5 \\ | \quad\quad \diagup \\ -N-N \\ \quad\quad \diagdown \\ \quad\quad\quad R^6 \end{array}$$

wherein R⁴, R⁵ and R⁶ may be the same of different and are hydrogen, alkyl, hydroxyalkyl, alkoxyalkyl, aminoalkyl or acylaminoalkyl where the carbon-containing portions contain from 1 to about 6 carbon atoms, or R⁵ and R⁶ joined together with the adjacent nitrogen form a heterocyclic ring of five, six or seven members, wherein 0 to 1 members other than the nitrogen are $$\begin{array}{ccccc} & & & O & & \\ & & & \| & & \\ -O-, & -S-, & -S-, & \text{or} & -N- \\ & & & \| & & | \\ & & & O & & R^7 \end{array}$$

and which members are unsubstituted or substituted by hydroxy, alkyl, aryl, hydroxyalkyl, aminoalkyl, aminoaryl, alkylamino, or carbamoyl, wherein the substituents contain from 1 to about 6 carbon atoms, or R⁴ and R⁵ joined together with the nitrogens to which each is attached form a heterocyclic ring of five, six or seven members, wherein 0 or 1 members other than the nitrogens are $$\begin{array}{ccccc} & & & O & & \\ & & & \| & & \\ -O-, & -S-, & -S-, & \text{or} & -N- \\ & & & \| & & | \\ & & & O & & R^7 \end{array}$$

and which members are unsubstituted or substituted by hydroxy, alkyl, aryl, hydroxyalkyl, aminoalkyl, aminoaryl, alkylamino, or carbamoyl wherein the substituents contain from 1 to about 6 carbon atoms;

R² and R³ may be the same or different and are hydrogen, alkyl having from 1 to about 6 carbon atoms, phenyl or benyzl;

R⁷ is hydrogen, alkyl, hydroxylalkyl, alkoxyalkyl, aminoalkyl or acylaminoalkyl wherein the carbon-containing portions contain from 1 to about 6 carbon atoms;

and wherein 2 or 3 of the R¹ groups are —O⁻ and the remainder of the R¹ groups are $$\begin{array}{c} R^4 \quad R^5 \\ | \quad\quad \diagup \\ -N-N \\ \quad\quad \diagdown \\ \quad\quad\quad R^6 \end{array} ;$$

and then exposing the animal to an NMR imaging procedure, thereby imaging at least a portion of the body of the warm-blooded animal.

13. The method of claim 12, wherein A is $$\begin{array}{c} \quad\quad\quad O \\ \quad\quad\quad \| \\ \quad CH_2-C-R^1 \\ \quad | \\ -CH_2CH_2NCH_2CH_2- \end{array}$$

14. The method of claim 12, wherein A is —CHR²CHR³— and R² and R³ are both hydrogen.

15. The method of claim 12, wherein $M^{+Z}$ is chromium (III), manganese (II), manganese (III), iron (III), iron (II), cobalt (II), nickel (II), copper (II), praseodymium (III), neodymium (III), samarium (III), ytterbium (III), gadolinium (III), terbium (III), dysprosium (III), holmium (III) or erbium (III).

16. The method of claim 15, wherein $M^{+Z}$ is gadolinium (III), terbium (III), dysprosium (III), holmium (III) or erbium (III).

17. The method of claim 16, wherein $R^1$ is dimethylhydrazide and $M^{+Z}$ is gadolinium (III).

18. The method of claim 17, wherein the pharmaceutically acceptable carrier contains a pharmaceutically acceptable buffer.

19. The method of claim 17, wherein the pharmaceutically acceptable carrier contains a pharmaceutically acceptable electrolyte.

* * * * *

UNITED STATES PATENT AND TRADEMARK OFFICE
CERTIFICATE OF CORRECTION

PATENT NO. : 5,384,108
DATED : January 24, 1995
INVENTOR(S) : Raghavan Rajagopalan It is certified that error appears in the above-indentified patent and that said Letters Patent is hereby corrected as shown below:

On the title page: item [57]:
<u>In the Abstract:</u> Line 9, after "42-44" insert a comma;
Col. 4, line 15, "Wherein" should be -- wherein --; Col. 5, line 30, the chemical compound should be --

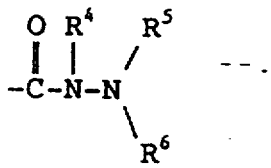

--.

Signed and Sealed this

Twenty-fifth Day of July, 1995

*Attest:*

BRUCE LEHMAN

*Attesting Officer*      *Commissioner of Patents and Trademarks*